United States Patent [19]

Loeffler et al.

[11] Patent Number: 4,569,930
[45] Date of Patent: Feb. 11, 1986

[54] 2-FLUOROPHENYL(DI)THIOPHOSPHATES AND THEIR USE IN PEST CONTROL

[75] Inventors: Hans-Peter Loeffler; Walter Seufert, both of Ludwigshafen; Heinrich Adolphi, Limburgerhof, all of Fed. Rep. of Germany

[73] Assignee: BASF Aktiengesellschaft, Fed. Rep. of Germany

[21] Appl. No.: 577,376

[22] Filed: Feb. 6, 1984

Related U.S. Application Data

[63] Continuation of Ser. No. 305,849, Sep. 25, 1981.

[30] Foreign Application Priority Data

Oct. 16, 1980 [DE] Fed. Rep. of Germany ....... 3039086

[51] Int. Cl.⁴ ..................... A01N 57/14; C07F 9/165
[52] U.S. Cl. .................................... 514/147; 260/964; 260/940; 260/949; 260/951; 260/954
[58] Field of Search ............... 260/964, 940, 949, 954; 514/147

[56] References Cited

U.S. PATENT DOCUMENTS 3,839,511 6/1974 Kishino et al. ..................... 260/964

FOREIGN PATENT DOCUMENTS 0022954 1/1981 European Pat. Off. ............ 260/964

Primary Examiner—Anton H. Sutto
Attorney, Agent, or Firm—Keil & Weinkauf

[57] ABSTRACT

2-Fluorophenyl(di)thiophosphates of the formula

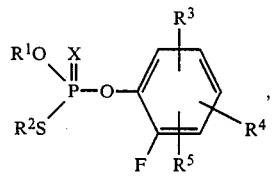

where $R^1$ is alkyl of 1 to 3 carbon atoms, $R^2$ is alkyl or haloalkyl of 1 to 5 carbon atoms, alkoxyalkyl or alkylthioalkyl of 2 to 6 carbon atoms or cycloalkyl of 3 to 6 carbon atoms, $R^3$, $R^4$ and $R^5$ independently of one another are hydrogen, halogen, cyano, nitro or alkyl, alkoxy or alkylthio of 1 to 4 carbon atoms and X is oxygen or sulfur, and their use in pest control.

8 Claims, No Drawings

2-FLUOROPHENYL(DI)THIOPHOSPHATES AND THEIR USE IN PEST CONTROL

This is a continuation, of application Ser. No. 305,849, filed Sept. 25, 1981, abandoned.

The present invention relates to 2-fluorophenyl(di)-thiophosphates, pest control agents which contain these compounds as the active ingredients, and a method of pest control using these active ingredients.

German Published Application DAS No. 2,1DAS 2,163,391 discloses O,S-dialkyl O-halophenyl-thiophosphates which are useful for the control of pests such as insects, arachnids and nematodes. However, fluorophenyl-thiophosphates are not described in that DAS.

We have found that 2-fluorophenyl(di)thiophosphates of the formula I

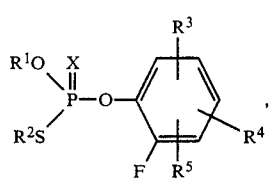
(I)

where $R^1$ is alkyl of 1 to 3 carbon atoms, $R^2$ is alkyl or haloalkyl of 1 to 5 carbon atoms, alkoxyalkyl or alkylthioalkyl of 2 to 6 carbon atoms or cycloalkyl of 3 to 6 carbon atoms, $R^3$, $R^4$ and $R^5$ independently of one another are hydrogen, halogen, cyano, nitro or alkyl, alkoxy or alkylthio of 1 to 4 carbon atoms and X is oxygen or sulfur, effectively control pests of the insect, arachnid and nematode classes. Their effect is superior to that of the known O,S-dialkyl O-halophenyl-thiophosphates of similar structure.

In formula I, $R^1$ is alkyl of 1 to 3 carbon atoms, e.g. methyl, ethyl, n-propyl or i-propyl, preferably ethyl, $R^2$ is alkyl or haloalkyl of 1 to 5 carbon atoms, e.g. ethyl, n-propyl, i-propyl, n-butyl, sec.-butyl, i-butyl, n-pentyl, 1-methyl-n-butyl, 3-methyl-n-pentyl, 2-chloroethyl or 3-chloro-n-propyl, alkoxyalkyl or alkylthioalkyl of 2 to 6 carbon atoms, e.g. 2-methoxyethyl, 2-ethoxyethyl, 2-isopropoxyethyl, 2-methylthioethyl or 2-ethylthioethyl, or cycloalkyl of 3 to 6 carbon atoms, e.g. cyclopentyl or cyclohexyl, and $R^3$, $R^4$ and $R^5$, which can be different, are each hydrogen, halogen, e.g. chlorine, bromine or fluorine, nitro or cyano, or alkyl, alkoxy or alkylthio of 1 to 4 carbon atoms, preferably methyl or ethyl. Preferably, $R^2$ is alkyl of 3 or 4 carbon atoms, e.g. n-propyl, isobutyl or sec.-butyl, $R^3$ is hydrogen, $R^4$ is halogen, such as chlorine or bromine, in the 4-position and $R^5$ is hydrogen.

The 2-fluorophenyl(di)thiophosphates of the formula I are obtained by reacting an O,S-dialkyl phosphate-chloride of the formula II

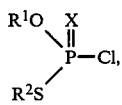
(II)

where $R^1$, $R^2$ and X have the above meanings, with a 2-fluorophenol of the formula III

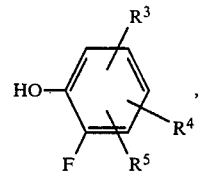
(III)

where $R^3$, $R^4$ and $R^5$ have the above meanings, in the presence or absence of an acid acceptor and in the presence or absence of a diluent, or with a salt of a 2-fluorophenol of the formula III in the presence or absence of a diluent.

The course of the reaction can be represented by the following equation:

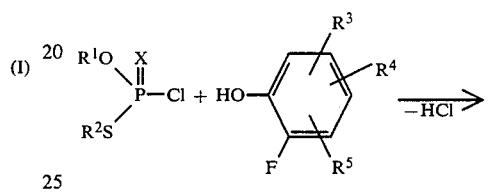

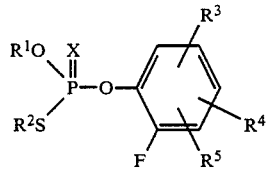

The reaction of the phosphate-chloride of the formula II with the phenol of the formula III can be carried out in an organic diluent, such as acetonitrile, toluene or methyl ethyl ketone, or in a two-phase system, such as toluene/water or methylene chloride/water.

Advantageously, 1-2 moles of an acid acceptor are added per mole of the phenol of the formula III. An excess of about 10% is preferably used. Suitable acid acceptors are bases, such as alkali metal carbonates, e.g. potassium carbonate, alkali metal hydroxides, e.g. sodium hydroxide, or tertiary amines, e.g. triethylamine. Instead of using the base and phenol, it is possible to react the phosphate-chloride with a salt of the phenol, for example an alkali metal salt, alkaline earth metal salt or substituted or unsubstituted ammonium salt, such as the sodium, potassium, calcium or alkylammonium salt.

The reaction can be carried out within a substantial temperature range, which is generally from room temperature to 100° C., preferably from 30° to 70° C., and usually proceeds under atmospheric pressure.

The starting substances are used in equimolar amounts, but an excess of one or other of the reactants can be advantageous in some cases. Preferably, from 0.9 to 1.1 moles of phosphate-chloride are used per mole of phenol.

The reaction mixture is worked up in a conventional manner, for example by adding water and separating the phases. The crude products can be purified by distillation or column chromatography.

O,S-Dialkyl phosphate-chlorides are known, and they can be prepared in a conventional manner (German Laid-Open Application DOS No. 2,642,982; and J. Org. Chem. 30 (1965), 3217). The 2-fluorophenols of the formula III can also be prepared in a conventional manner (U.S. Pat. No. 3,794,734 and French Patent No. 2,234,261).

The processes below also lead to the compounds according to the invention:

2-Fluorophenyl thiophosphates of the formula Ia can be prepared in an Arbusow reaction between a phosphite of the formula IV and a sulfenyl chloride of the formula $R^2SCl$ in accordance with the following equation:

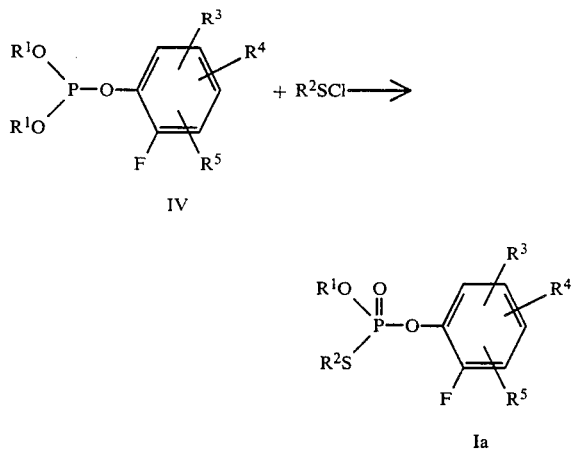

The 2-fluorophenyl thiophosphates of the formula Ia can also be obtained by alkylating a thiophosphate salt of the formula V with an alkylating agent of the formula $R^2Y$:

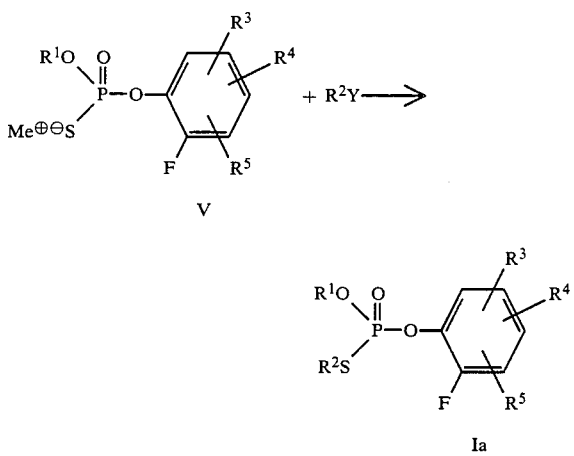

Furthermore, phosphate-dichlorides of the formula VI can be reacted with alcohols and mercaptans of the formula $R^1OH$ or $R^2SH$ to give compounds of the formula I:

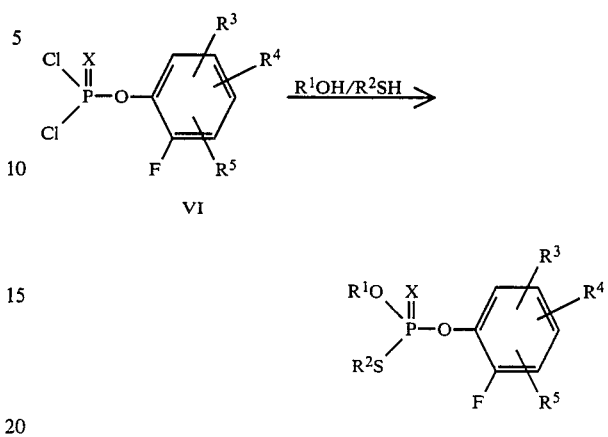

In these equations, $R^1$, $R^2$, $R^3$, $R^4$, $R^5$ and X have the above meanings. $Me^\oplus$ is a metal cation or an ammonium ion which is unsubstituted or substituted by alkyl, and Y is halide, for example iodide, bromide or chloride, or alkyl-sulfate, for example methyl-sulfate.

PREPARATION EXAMPLE 10.3 ml of bromine are added dropwise to 22.4 g of 2-fluorophenol in 100 ml of methylene chloride at $-20°$ C. The mixture is left to stand for 48 hours, after which the solution is colorless. After stripping off the solvent, 34 g of 4-bromo-2-fluorophenol are obtained; $n_D^{24}=1.5645$.

5.5 g of potassium carbonate are added to 7.5 g of the resulting 4-bromo-2-fluorophenol in 100 ml of acetonitrile and the mixture is refluxed for one hour, with stirring. 7.5 g of O-ethyl S-n-propyl thiophosphate-chloride are then added dropwise at 50° C. and the mixture is stirred at this temperature for 3 hours and then at room temperature for 24 hours. The solvent is removed on a rotary evaporator, 400 ml of toluene and 100 ml of water are added, the phases are separated, the organic phase is washed with 2N sodium hydroxide solution and then with water and is dried with sodium sulfate, and the solvent and volatile impurities are stripped off under reduced pressure at 40° C./0.13 mbar. 7.5 g of O-ethyl S-n-propyl O-(4-bromo-2-fluorophenyl) thiophosphate are obtained as the residue; $n_D^{21}=1.5269$.

The following compounds can be prepared, for instance, by a process similar to this Example or by one of the processes described above:

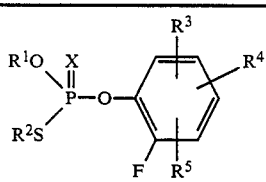

| No. | $R^1$ | $R^2$ | X | $R^3$ | $R^4$ | $R^5$ | $n_D$ |
|---|---|---|---|---|---|---|---|
| 1 | $CH_3$ | $n-C_3H_7$ | S | H | H | H | |
| 2 | $CH_3$ | $n-C_3H_7$ | O | H | H | H | |
| 3 | $CH_3$ | $sec-C_4H_9$ | S | H | H | H | |
| 4 | $CH_3$ | $sec-C_4H_9$ | O | H | H | H | |
| 5 | $CH_3$ | $n-C_3H_7$ | O | H | 4-Br | H | |

-continued

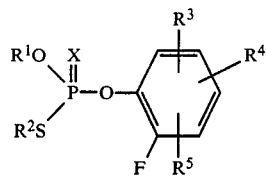

| No. | R¹ | R² | X | R³ | R⁴ | R⁵ | $n_D$ |
|---|---|---|---|---|---|---|---|
| 6 | CH₃ | n-C₃H₇ | O | H | 4-Cl | H | |
| 7 | CH₃ | sec-C₄H₉ | O | 6-Cl | H | H | |
| 8 | CH₃ | n-C₃H₇ | O | H | H | 3-Cl | |
| 9 | C₂H₅ | CH₃ | O | H | H | H | |
| 10 | C₂H₅ | n-C₃H₇ | O | H | 4-Cl | H | |
| 11 | C₂H₅ | n-C₃H₇ | O | H | 4-Br | H | $n_D^{24} = 1.5366$ |
| 12 | C₂H₅ | n-C₃H₇ | O | 6-Cl | H | H | |
| 13 | C₂H₅ | n-C₃H₇ | O | 6-Cl | 4-Cl | H | |
| 14 | C₂H₅ | n-C₃H₇ | O | H | H | H | $n_D^{25} = 1.5025$ |
| 15 | C₂H₅ | n-C₃H₇ | O | H | 4-Cl | H | $n_D^{24} = 1.5121$ |
| 16 | C₂H₅ | n-C₃H₇ | O | H | 4-Br | H | $n_D^{21} = 1.5269$ |
| 17 | C₂H₅ | n-C₃H₇ | O | H | 4-F | H | |
| 18 | C₂H₅ | n-C₃H₇ | O | 6-Cl | H | H | |
| 19 | C₂H₅ | n-C₃H₇ | O | 6-Br | H | H | |
| 20 | C₂H₅ | n-C₃H₇ | O | 6-Cl | 4-Cl | H | |
| 21 | C₂H₅ | n-C₃H₇ | O | H | 4-CN | H | |
| 22 | C₂H₅ | n-C₃H₇ | S | H | H | H | $n_D^{28} = 1.5383$ |
| 23 | C₂H₅ | n-C₃H₇ | S | H | 4-Cl | H | $n_D^{24} = 1.5489$ |
| 24 | C₂H₅ | n-C₃H₇ | S | H | 4-Br | H | $n_D^{22} = 1.5620$ |
| 25 | C₂H₅ | n-C₃H₇ | S | H | 4-F | H | |
| 26 | C₂H₅ | n-C₃H₇ | S | 6-Cl | H | H | |
| 27 | C₂H₅ | n-C₃H₇ | S | 6-Br | H | H | |
| 28 | C₂H₅ | n-C₃H₇ | S | 6-Cl | 4-Cl | H | |
| 29 | C₂H₅ | n-C₃H₇ | S | H | 4-CN | H | |
| 30 | C₂H₅ | n-C₃H₇ | S | 6-Br | 4-Br | H | |
| 31 | C₂H₅ | i-C₃H₇ | O | H | H | H | |
| 32 | C₂H₅ | i-C₃H₇ | O | H | 4-Cl | H | |
| 33 | C₂H₅ | i-C₃H₇ | O | H | 4-Br | H | |
| 34 | C₂H₅ | i-C₃H₇ | S | H | H | H | |
| 35 | C₂H₅ | i-C₃H₇ | S | H | 4-Cl | H | |
| 36 | C₂H₅ | i-C₃H₇ | S | H | 4-Br | H | |
| 37 | C₂H₅ | i-C₃H₇ | S | H | H | 4-CN | |
| 38 | C₂H₅ | sec-C₄H₉ | O | H | H | H | $n_D^{22} = 1.5003$ |
| 39 | C₂H₅ | sec-C₄H₉ | O | H | 4-Cl | H | $n_D^{26} = 1.5079$ |
| 40 | C₂H₅ | sec-C₄H₉ | O | H | 4-Br | H | $n_D^{24} = 1.5238$ |
| 41 | C₂H₅ | sec-C₄H₉ | O | H | 4-CN | H | |
| 42 | C₂H₅ | sec-C₄H₉ | O | H | 4-F | H | |
| 43 | C₂H₅ | sec-C₄H₉ | O | 6-Cl | 4-Cl | H | |
| 44 | C₂H₅ | sec-C₄H₉ | O | 6-Br | 4-Br | H | |
| 45 | C₂H₅ | sec-C₄H₉ | S | H | H | H | $n_D^{29} = 1.5335$ |
| 46 | C₂H₅ | sec-C₄H₉ | S | H | 4-Cl | H | $n_D^{23} = 1.5440$ |
| 47 | C₂H₅ | sec-C₄H₉ | S | H | 4-Br | H | $n_D^{25} = 1.5559$ |
| 48 | C₂H₅ | sec-C₄H₉ | S | H | 4-F | H | |
| 49 | C₂H₅ | sec-C₄H₉ | S | H | H | 4-CN | |
| 50 | C₂H₅ | sec-C₄H₉ | S | 6-Cl | 4-Cl | H | |
| 51 | C₂H₅ | sec-C₄H₉ | S | 6-Br | 4-Br | H | |
| 52 | C₂H₅ | i-C₄H₉ | O | H | H | H | $n_D^{24} = 1.5010$ |
| 53 | C₂H₅ | i-C₄H₉ | O | H | 4-Cl | H | $n_D^{22} = 1.5086$ |
| 54 | C₂H₅ | i-C₄H₉ | O | H | 4-Br | H | $n_D^{21} = 1.5215$ |
| 55 | C₂H₅ | i-C₄H₉ | O | H | 4-CN | H | |
| 56 | C₂H₅ | i-C₄H₉ | O | 6-Br | 4-Br | H | |
| 57 | C₂H₅ | i-C₄H₉ | O | H | 4-F | H | |
| 58 | C₂H₅ | i-C₄H₉ | O | 6-Cl | 4-Cl | H | |
| 59 | C₂H₅ | i-C₄H₉ | S | H | H | H | |
| 60 | C₂H₅ | i-C₄H₉ | S | H | 4-Cl | H | $n_D^{23} = 1.5418$ |
| 61 | C₂H₅ | i-C₄H₉ | S | H | H | 4-Br | |
| 62 | C₂H₅ | i-C₄H₉ | S | H | 4-CN | H | |
| 63 | C₂H₅ | i-C₄H₉ | S | 6-Br | H | 4-Br | |
| 64 | C₂H₅ | i-C₄H₉ | S | H | 4-F | H | |
| 65 | C₂H₅ | i-C₄H₉ | S | 6-Cl | 4-Cl | H | |
| 66 | C₂H₅ | CH₃O—(CH₂)₂— | O | H | H | H | $n_D^{27} = 1.5061$ |
| 67 | C₂H₅ | CH₃O—(CH₂)₂— | O | H | H | 4-Cl | $n_D^{26} = 1.5141$ |
| 68 | C₂H₅ | CH₃O—(CH₂)₂— | O | H | 4-Br | H | $n_D^{28} = 1.5275$ |
| 69 | C₂H₅ | CH₃O—(CH₂)₂— | O | H | 4-CN | H | |
| 70 | C₂H₅ | CH₃O—(CH₂)₂— | O | 6-Br | 4-Br | H | |
| 71 | C₂H₅ | C₂H₅O—(CH₂)₂— | O | H | H | H | |
| 72 | C₂H₅ | C₂H₅O—(CH₂)₂— | O | H | 4-Cl | H | |
| 73 | C₂H₅ | C₂H₅O—(CH₂)₂— | O | H | 4-Br | H | $n_D^{28} = 1.5228$ |
| 74 | C₂H₅ | C₂H₅O—(CH₂)₂— | O | H | 4-CN | H | |
| 75 | C₂H₅ | C₂H₅O—(CH₂)₂— | O | 6-Br | 4-Br | H | |
| 76 | C₂H₅ | C₂H₅O—(CH₂)₂— | O | 6-Cl | 4-Cl | H | |

-continued

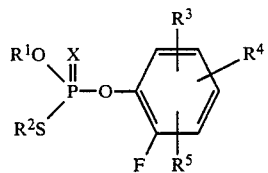

| No. | R$^1$ | R$^2$ | X | R$^3$ | R$^4$ | R$^5$ | n$_D$ |
|---|---|---|---|---|---|---|---|
| 77 | C$_2$H$_5$ | i-C$_3$H$_7$O—(CH$_2$)$_2$— | O | H | H | H | |
| 78 | C$_2$H$_5$ | i-C$_3$H$_7$O—(CH$_2$)$_2$— | O | H | 4-Cl | H | n$_D^{21}$ = 1.5050 |
| 79 | C$_2$H$_5$ | i-C$_3$H$_7$O—(CH$_2$)$_2$— | O | H | 4-Br | H | n$_D^{22}$ = 1.5159 |
| 80 | C$_2$H$_5$ | i-C$_3$H$_7$O—(CH$_2$)$_2$— | O | H | 4-CN | H | |
| 81 | C$_2$H$_5$ | i-C$_3$H$_7$O—(CH$_2$)$_2$— | O | 6-Br | 4-Br | H | |
| 82 | C$_2$H$_5$ | i-C$_3$H$_7$O—(CH$_2$)$_2$— | O | 6-Cl | 4-Cl | H | |
| 83 | C$_2$H$_5$ | C$_5$H$_9$ | O | H | H | H | |
| 84 | C$_2$H$_5$ | C$_5$H$_9$ | O | H | 4-Cl | H | |
| 85 | C$_2$H$_5$ | C$_5$H$_9$ | O | H | 4-Br | H | |
| 86 | C$_2$H$_5$ | C$_5$H$_9$ | O | H | 4-Br | H | |
| 87 | C$_2$H$_5$ | C$_5$H$_9$ | S | H | 4-Cl | H | |
| 88 | C$_2$H$_5$ | C$_5$H$_9$ | S | H | H | 4-Br | |
| 89 | C$_2$H$_5$ | CH$_3$—(CH$_2$)$_2$—CH(CH$_3$)— | O | H | H | H | |
| 90 | C$_2$H$_5$ | CH$_3$—(CH$_2$)$_2$—CH(CH$_3$)— | O | H | H | 4-Cl | |
| 91 | C$_2$H$_5$ | CH$_3$—(CH$_2$)$_2$—CH(CH$_3$)— | O | H | H | 4-Br | |
| 92 | C$_2$H$_5$ | ClCH$_2$—(CH$_2$)$_2$— | O | H | H | H | |
| 93 | C$_2$H$_5$ | ClCH$_2$—(CH$_2$)$_2$— | O | H | 4-Cl | H | |
| 94 | C$_2$H$_5$ | ClCH$_2$—(CH$_2$)$_2$— | O | H | 4-Br | H | n$_D^{22}$ = 1.5389 |
| 95 | C$_2$H$_5$ | ClCH$_2$—(CH$_2$)$_2$— | O | H | 4-CN | H | |
| 96 | C$_2$H$_5$ | CH$_3$S—CH$_2$— | O | H | H | H | n$_D^{22}$ = 1.5420 |
| 97 | C$_2$H$_5$ | C$_2$H$_5$S—(CH$_2$)$_2$— | O | H | H | H | n$_D^{22}$ = 1.5315 |
| 98 | C$_2$H$_5$ | CH$_3$S—(CH$_2$)$_2$— | O | H | H | H | n$_D^{20}$ = 1.5385 |
| 99 | C$_2$H$_5$ | CH$_3$S—CH$_2$— | O | H | 4-Cl | H | n$_D^{20}$ = 1.5485 |
| 100 | n-C$_3$H$_7$ | C$_2$H$_5$ | O | H | 4-Cl | H | n$_D^{24}$ = 1.5109 |

The 2-fluorophenyl(di)thiophosphates of the formula I according to the invention are suitable for effectively combating pests from the classes of insects, arachnids and nematodes. They may be employed as pesticides for protecting crops, and in the hygiene, stores protection and veterinary sectors.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus piniarus, Hyphantria cunea, Agrotis segetum, Agrotis ypsilon, Barathra brassicae, Cirphis unipuncta, Prodenia litura, Laphygma exigua, Panolis flammea, Earias insulana, Plusia gamma, Alabama argillacea, Lymantria dispar., Lymantria monocha, Pieris brassicae,* and *Aporia crataegi;* examples from the Coleoptera order are *Blitophaga undata, Melanotus communis, Limonius californicus, Agriotes lineatus, Agricotes obscurus, Agrilus sinuatus, Meligethes aeneus, Atomaria linearis, Epilachna varivestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;* examples from the Diptera order are *Lycoria pectoralis, Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae, Pegomya hyoscyami, Anopheles maculipennis, Culex pipiens, Aedes aegypti, Aedes vexans, Tabanus bovinus, Tipula paludosa, Musca domestica, Fannia canicularis, Muscina stabulans, Glossina morsitans, Oestrus ocis, Chrysomya macellaria, Chrysomya hominivorax, Lucilia cuprina, Lucilia sercata,* and *Hypoderma lineata;* examples from the Hymenoptera order are *Athalia rosae, Haplocampa minuta, Monomorium pharaonis, Solenopsis geminata,* and *Atta sexdens;* examples from the Heteroptera order are *Nezara viridula, Eurygaster integriceps, Blissus leucopterus, Dysdercus cingulatus, Dysdercus intermedius, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;* examples from the Isoptera order is *Reticulitermes lucifugus, Leucotermes flavipes,* and *Terms natalensis;* examples from the Orthoptera order are *Forficula auricularia, Acheta domestica, Gryllotalpa gryllotalpa, Tachycines asynamorus, Locusta migratoria, Stauronotus maroccanus, Schistocerca peregrina, Nomadacris septemfasciata, Melanoplus spretus, Melanoplus femur-rubrum, Blatta orientalis, Blattella germanica, Periplaneta americana,* and *Blabera gigantea.*

Examples of mites and ticks (Acarina) belonging to the Arachnida class are *Tetranychus telarius, Tetranychus atlanticus, Tetranychus pacificus, Paratetranychus pilosus, Bryobia praetiosa, Ixodes ricinus, Ornithodorus moubata, Ablyomma americanum, Dermacentor silvarum,* and *Boophilus microplus.*

Examples from the Nemathelminthes class are root-knot nematodes, e.g., *Meloidogyne incognita, Meloidogyne hapla,* and *Meloidogyne javanica,* cyst-forming nematodes, e.g., *Heterodera rostochiensis, Heterodera schachtii, Heterodera avenae, Heterodera glycines,* and *Heterodera trifolii,* and stem and leaf eelworms, e.g., *Ditylenchus dipsaci, Ditylenchus destructor, Pratylenchus neglectus, Pratylenchus penetrans, Pratylenchus goodeyi, Pratylenchus curvitatus* and *Tylenchorhynchus dubius, Tylenchorhynchus claytoni, Rotylenchus robustus, Heliocotylenchus multicinctus, Radopholus similis, Belonolaimus longicaudatus, Longidorus elongatus,* and *Trichodorus primitivus.*

The active ingredients may be applied as such, in the form of formulations, or of ready-to-use application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, and strongly polar solvents such as dimethylformamide, dimethylsulfoxide, N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalene-sulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyester alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Examples of formulations are given below.

I. 5 parts by weight of compound no. 14 is intimately mixed with 95 parts by weight of particulate kaolin. A dust is obtained containing 5% by weight of the active ingredient.

II. 30 parts by weight of compound no. 15 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. 23 is dissolved in a mixture consisting of 90 parts by weight of xylene, 6 parts by weight of the adduct of 8 to 10 moles of ethylene oxide with 1 mole of oleic acid-N-monoethanolamide, 2 parts by weight of the calcium salt of dodecylbenzenesulfonic acid, and 2 parts by weight of the adduct of 40 moles of ethylene oxide with 1 mole of castor oil.

IV. 20 parts by weight of compound no. 24 is dissolved in a mixture consisting of 60 parts by weight of cyclohexanone, 30 parts by weight of isobutanol, 5 parts by weight of the adduct of 7 moles of ethylene oxide with 1 mole of isooctylphenol, and 5 parts by weight of the adduct of 40 moles of ethylene oxide with 1 mole of castor oil.

V. 80 parts by weight of compound no. 52 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate ammonium nitrate, and ureas, and vegetable products such as grain flours, bark meal, wood meal, and nutshell meal, cellulosic powders, etc.

The formulations generally contain from 0.1 to 95, and preferably 0.5 to 90%, by weight of active ingredient.

The amount of active ingredient in the ready-to-use formulations may vary within a wide range; it is generally from 0.0001 to 10%, preferably from 0.01 to 1%.

The active ingredients may also be successfully used in the ultra-low volume method, where it is possible to apply formulations containing more than 95 wt % of active ingredient, or even the 100% active ingredient.

When the active ingredient are applied in the open, the rates are from 0.2 to 10, preferably 0.5 to 2.0, kg/ha.

There may be added to the active ingredients (if desired, immediately before use (tankmix)) oils of various types, herbicides, fungicides, other insecticides and bactericides. These agents may be added to the active ingredients according to the invention in a weight ratio of from 1:10 to 10:1.

Examples of active ingredients which may be admixed are as follows: 1,2-dibromo-3-chloropropane, 1,3-dichloropropene, 1,3-dichloropropene+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro--dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propionaldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N'N'-dimethylformamidine, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p nitrophenyl)-phosphorothioate, O-ethyl-O-(p-nitrophenyl)-phenylphosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethylphosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5-onyl-(4)-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6methyl-4-pyrimidinyl]-thionophosphate, O,O-dimethyl-S-(4-oxo-1,2,3-benzotriazin 3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl-thionophosphate, 1 -yl)-thionophosphate, O,S-dimethylphosphoroamidothioate, O,S-dimethyl-N-acetylphosphoramidothioate, γ-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-allyl-3-methylcyclopenten-(2)-on-(1)-yl-(4)-DL-cis,trans-chrysanthemate, 5-benzylfuryl-(3)-methyl-DL-cis,trans-chrysanthemate, 3-phenoxybenzyl($\pm$)-cis,trans-2,2-dimethyl-3-(2,2-dichlorovinyl)-cyclopropanecarboxylate, α-cyano-3-phenoxybenzyl($\pm$)-cis,trans-2,2-dimethyl-3-(2,2-dichlorovinyl)-cyclopropane carboxylate, (s)-α-cyano-3-phenoxybenzyl-cis(1R,3R)-2,2-dimethyl-3-(2,2-dibromovinyl)-cyclopropane carboxylate, 3,4,5,6-tetrahydrophthalimidoethyl-DL-cis,trans-chrysanthemate, 2-methyl-5-(2-propynyl)-3-furylmethyl-chrysanthemate, and α-cyano 3-phenoxybenzyl-α-isopropyl-4-chlorophenylacetate.

The following examples illustrate the biological action of the compounds of the formula I. The prior art active ingredient used for comparison purposes is O-ethyl-S-n-propyl-O-(2,4-dichlorophenyl)-thiophosphate (German Published Application DAS No.2,163,391).

The active ingredients are numbered as in the foregoing table.

EXAMPLE 1

CONTACT ACTION on HOUSEFLIES (*Musca domestica*)

1 μl of acetonic solutions of the active ingredients are administered by means of a micro-syringe to the ventral abdomen of 4-day-old imagoes under slight $CO_2$ narcosis. 20 animals treated in the same manner are then placed in a plastic bag (approx. 500 ml).

After 4 days, the animals in supine position are counted and the $LD_{50}$ is determined by means of a graph. In this test, the following active ingredients have a very good action: 14, 15, 16, 22, 23, 24, 38, 39, 40, 45, 47, 52, 53 and 54.

EXAMPLE 2

Contact Action on Bean Aphids (*Aphis fabae*); Spray Experiment

Potted bean plants (*Vicia faba*) with extensive aphid colonies are sprayed to runoff in a spray booth with aqueous formulations of the active ingredients. Assessment takes place after 48 hours.

In this test, for example compounds nos. 14, 15, 16, 22, 23, 24, 38, 39, 40, 52, 53, 54, 60, 66, 67 and 73 have a better action than the comparative agent.

EXAMPLE 3

Contact Action and the Effect of Ingested Food on Caterpillars of the Diamondback Moth (*Plutella maculipennis*)

Leaves of young cabbage plants are dipped for 3 seconds in aqueous emulsions of the active ingredients, and, after briefly having allowed excess liquid to drip off, are placed on a moist filter paper in a Petri dish. 10 caterpillars of the 4th stage are then placed on the leaves. The action is assessed after 48 hours.

In this test, for example the following active ingredients have an action superior to that of the art: 14, 15, 16, 22, 23, 24, 38, 39, 40, 45, 46, 47, 52, 53, 54, 78 and 79.

EXAMPLE 4

Contact Action on Mosquito Larvae (*Aedes aegypti*)

Aqueous formulations of the active ingredients are added to 200 ml of tapwater, 30 to 40 mosquito larvae in the 4th larval stage are then introduced. The temperature is kept at 20° C. The action is assessed after 25 hours.

In this test, for example active ingredients nos, 22, 38, 39 and 45 have a better action than the comparative agent.

EXAMPLE 5

Contact Action on Oriental Cockroaches (*Blatta orientalis*)

The bottoms of 1 liter preserving jars is lined with acetonic solutions of the active ingredients. After the solvent has evaporated, 5 adult cockroaches are introduced into each jar. The kill rate is determined after 48 hours.

In this test, active ingredients nos. 14, 15, 16, 22, 23, 24, 38, 39, 40, 45, 46, 52, 53, 54, 60, 66, 73 and 78 have a better action than the comparative agent.

EXAMPLE 6

Contact Action on Granary Weevils (*Sitophilus granarius*)

Petris dishes 10 cm in diameter are lined with acetonic solutions of the active ingredients. After the solvent has evaporated, 100 granary weevils are placed in each dish.

After 4 hours, the weevils are transferred to untreated vessels. The kill rate is determined after 24 hours, by counting how many weevils are, after this period has elapsed, capable of leaving an untreated cardboard dish (40 mm in diameter, 10 mm high) within 60 minutes.

The kill rate after treatment with active ingredients nos. 14, 15, 22, 23, 24, 38, 39, 40, 45, 52, 53, 66, 68, 73, 78 and 79 is much higher, with comparable amounts of active ingredient per Petri dish, than after treatment with the comparative agent.

EXAMPLE 7

Contact Action on Ticks (*Ornithodorus moubata*)

Ticks in the 3rd larval stage are placed in paper bags and dipped for 3 seconds in the emulsion under investigation. The bags are then suspended. The action on the ticks is assessed after 48 hours.

In this test, a higher kill rate is achieved with emulsions having a lower concentration of active ingredients nos. 14, 15, 16, 38, 39, 40, 52, 53, 54, 60, 67, 73 and 78 than of the comparative agent.

EXAMPLE 8

Action on Root-Knot Nematodes (*Meloidogyne incognita*)

Young tomato plants are planted in 500 g of compost heavily infested with root-knot nematodes. Treatment is carried out after 3 days by spraying, in a booth, 50 ml of aqueous formulations of the active ingredients.

The roots are checked for root-knots after 6 to 8 weeks.

In this test, for example active ingredients nos. 22, 23, 46, 52, 60, 66, 72, 78 and 79 have a very good action.

EXAMPLE 9

Action on Spider Mites (*Tetranychus telarius*)

Potted bush beans which have developed the first pair of true leaves and are under heavy attack from spider mites (*Tetranychus telarius*) of all stages are sprayed to runoff from all sides in a spray cabinet with aqueous formulations of the active ingredients.

The plants are placed on a rotatable disc and are sprayed with 50 ml of spray liquor. Spraying lasts for about 22 seconds. The plants are investigated after 8 days for living spider mites.

In this test, active ingredients nos. 11, 14, 15, 16, 22, 24, 39, 40, 53, 54, 67, 78 and 79 have a better action than the comparative agent.

We claim:

1. A 2-fluorophenyl(di)thiophosphate of the formula $$\begin{array}{c} R^1O \\ \diagdown \\ R^2S \end{array} \overset{X}{\underset{\parallel}{P}} -O- \underset{F}{\underset{R^5}{\bigcirc}} \overset{R^3}{\underset{R^4}{}} \quad (I)$$

where $R^1$ is alkyl of 1 to 3 carbon atoms, $R^2$ is alkyl or haloalkyl of 1 to 5 carbon atoms, alkoxyalkyl or alkylthioalkyl of 2 to 6 carbon atoms or cycloalkyl of 3 to 6 carbon atoms, $R^3$, $R^4$ and $R^5$ independently of one another are chlorine, bromine, halogen, cyano, nitro or alkyl, alkoxy or alkylthio of 1 to 4 carbon atoms and X is oxygen or sulfur.

2. A 2-fluorophenyl(di)thiophosphate of the formula I as defined in claim 1, wherein $R^1$ is ethyl, $R^2$ is alkyl of 3 or 4 carbon atoms, $R^3$ is chlorine or bromine, $R^4$ is halogen, $R^5$ is hydrogen, and X is oxygen or sulfur.

3. O-Ethyl-S-n-propyl-O-(2-fluoro-4-chlorophenyl)-thiophosphate.

4. O-Ethyl-S-n-propyl-O-(2-fluoro-4-bromophenyl)-thiophosphate.

5. A pesticide comprising a solid or liquid carrier, and a 2-fluorophenyl(di)thiophosphate of the formula I as defined in claim 1.

6. A process for combating pests, wherein a 2-fluorophenyl(di)thiophosphate of the formula I as defined in claim 1 is allowed to act on the pests and/or their habitat.

7. A compound of the formula I as defined in claim 1, wherein $R^3$, $R^4$, and $R^5$ independently of one another are hydrogen, chlorine, bromine, cyano, nitro or alkoxy or alkylthio of 1 to 4 carbon atoms and X is oxygen or sulfur.

8. A compound of the formula as defined in claim' 1, wherein $R^1$ is alkyl or 1 to 3 carbon atoms, $R^2$ is alkyl of 1 to 5 carbon atoms, $R^3$ is hydrogen, $R^4$ is chlorine or bromine, $R^5$ is hydrogen and X is oxygen or sulfur.

* * * * *